(12) United States Patent
Gross

(10) Patent No.: US 6,353,148 B1
(45) Date of Patent: Mar. 5, 2002

(54) FRACTURE RESISTANT SUPERABSORBENT POLYMERS

(75) Inventor: James R. Gross, Cordova, TN (US)

(73) Assignee: BKI Holding Corporation, Wilmington, DE (US)

(*) Notice: Subject to any disclaimer, the term of this patent is extended or adjusted under 35 U.S.C. 154(b) by 0 days.

(21) Appl. No.: 09/216,686

(22) Filed: Dec. 18, 1998

Related U.S. Application Data

(60) Provisional application No. 60/088,452, filed on Jun. 8, 1998.

(51) Int. Cl.$^7$ .......................... A61F 13/15; A61L 15/42; A61L 15/60
(52) U.S. Cl. .................. 604/368; 604/365; 604/385.01; 604/385.22; 604/385.31; 524/379; 524/530; 524/831; 526/240
(58) Field of Search .................. 604/385.1, 385.01, 604/385.22, 385.31, 365, 368; 524/379, 831, 530; 526/240

(56) References Cited

U.S. PATENT DOCUMENTS

| | | | |
|---|---|---|---|
| 2,929,154 A | | 3/1960 | Finnegan |
| 3,224,986 A | | 12/1965 | Butler et al. |
| 3,332,909 A | | 7/1967 | Farnham et al. |
| 3,660,431 A | | 5/1972 | Hatch et al. |
| 3,669,103 A | | 6/1972 | Harper et al. |
| 3,749,738 A | | 7/1973 | Hatch et al. |
| 3,980,663 A | | 9/1976 | Gross |
| 4,056,103 A | * | 11/1977 | Kaczmarzyk et al. ....... 128/285 |
| 4,076,673 A | | 2/1978 | Burkholder |
| 4,084,033 A | * | 4/1978 | Drelich ......................... 428/198 |
| 4,596,567 A | | 6/1986 | Iskra |
| 4,645,789 A | | 2/1987 | Dabi |
| 4,721,647 A | | 1/1988 | Nakanishi et al. |
| 4,914,170 A | | 4/1990 | Chang et al. |
| 5,009,650 A | | 4/1991 | Bernardin |
| 5,041,104 A | | 8/1991 | Seal |
| 5,100,397 A | * | 3/1992 | Poccia et al. ................ 604/365 |
| 5,128,082 A | | 7/1992 | Makoui |
| 5,147,343 A | | 9/1992 | Kellenberger |
| 5,176,668 A | | 1/1993 | Bernardin |
| 5,268,419 A | | 12/1993 | Stack et al. |
| 5,336,554 A | | 8/1994 | Knight |
| 5,378,528 A | | 1/1995 | Makoui |
| 5,389,181 A | | 2/1995 | Vukos et al. |
| 5,522,810 A | | 6/1996 | Allen et al. |
| 5,607,414 A | | 3/1997 | Richards et al. |
| 5,645,542 A | * | 7/1997 | Anjur et al. ................. 604/368 |
| 5,844,039 A | | 12/1998 | Scranton et al. |
| 6,241,713 B1 | * | 6/2001 | Gross et al. ................. 604/368 |

FOREIGN PATENT DOCUMENTS

| | | |
|---|---|---|
| EP | 0 689 817 A2 | 1/1996 |
| EP | 0 690 077 A1 | 1/1996 |
| WO | WO 94/22940 A | 10/1994 |

OTHER PUBLICATIONS

Carr et al., Interpolymer from Starch Xanthate and Polyamide–Polyamine–Epichlorohydrin Resin: Structure and Papermaking Application, Journal of Applied Polymer Science, 17:721–735 (1973).

* cited by examiner

Primary Examiner—John G. Weiss
Assistant Examiner—Michael Bogart
(74) Attorney, Agent, or Firm—Darby & Darby

(57) ABSTRACT

The present invention is directed to a hydrogel-forming polymeric material including a first compound which is a superabsorbent polymer and a second compound present in the first as a dispersed phase including an elastomeric material effective to increase the fracture resistance of the superabsorbent. The material is prepared from a first compound including carboxylic-functional polyelectrolytes in combination with a crosslinkers reactive with carboxyl or carboxylate groups and an effective amount of a second compound including an aqueous dispersion of a rubbery material. In one preferred embodiment, the fracture resistant polymer is prepared from monomer/crosslinker solution mixed with latex.

16 Claims, No Drawings

FRACTURE RESISTANT SUPERABSORBENT POLYMERS

This application claims priority under 35 U.S.C. §119 from Provisional Application Ser. No. 60/088,452 filed Jun. 8, 1998 which is hereby incorporated herein in its entirety.

FIELD OF THE INVENTION

The present invention is directed to improved superabsorbent polymers demonstrating high fracture resistance. More particularly, the present invention is directed to improved superabsorbent polymers containing a dispersed phase comprising an elastomeric material. The resultant improved superabsorbent polymer is particularly useful in disposable personal care articles such as diapers, adult incontinence devices, and feminine napkins.

BACKGROUND OF THE INVENTION

Conventional absorbent articles such as baby diapers, adult incontinence devices, and feminine napkins are typically made with a cellulose fiber fluff-based absorbent core sandwiched between a liquid pervious top sheet whose function is to allow the unobstructed passage of fluid to the absorbent core, and a liquid impervious backing sheet, usually of plastic material, whose function is to contain the absorbed fluid and prevent it from passing through the absorbent core and soiling the undergarments of the wearer of the absorbent article.

The absorbent core of these absorbent articles is typically constructed of defiberized wood pulp combined with superabsorbent polymer granules. The absorbent core is typically formed on a carrier tissue in a pad forming unit of a converting machine. With regard to conventionally produced absorbent structures, reference is made to U.S. Pat. Nos. 5,009,650, 5,378,528, 5,128,082, 5,607,414, 5,147,343, 5,149,335, 5,522,810, 5,041,104, 5,176,668, 5,389,181, and 4,596,567, the disclosures of which are hereby incorporated herein by reference, as are the disclosures of all other patents, patent applications or references cited herein.

It is known from U.S. Pat. Nos. 3,669,103 and 3,670,731 that carboxylic polyelectrolytes may be crosslinked to create hydrogel-forming materials, now commonly referred to as superabsorbents, supersorbers or superabsorbent polymers (generally referred to herein as "SAPs"), and to employ such materials to enhance the absorbency of disposable absorbent articles. It is also known from U.S. Patent Nos. 3,980,663 and 4,076,673 that SAP may be formed by adding crosslinkers to solutions of carboxylated polyelectrolytes and then drying and curing the polymer. Unfortunately, the prior art approaches to making SAPs yield brittle, glassy, abrasive particulates. As a result, absorbent products generally incorporate SAPs in the form of discrete particles which may take the form of granules, flakes, powder, chunks, nuggets, pellets, needles, fibers, rods and the like. During further handling or processing, these brittle SAP materials tend to break into smaller particles, even dust particles that are small enough to become airborne. The fracture of SAP particles into smaller particles or dust creates an industrial hygiene problem. The airborne dust contaminates the air in the manufacturing and converting plants. In addition, small particles can foul the manufacturing and converting equipment. Sometimes fouling problems necessitate the incorporation of design features (such as carrier tissue) in the absorbent products simply to minimize the fouling of the equipment by small SAP particles. The brittleness of SAPs has traditionally poses a dusting problem not only while it is being processed into an absorbent article, but also in that the particle size distribution shifts toward smaller particles after the product leaves the manufacturer while it is being processed into an absorbent article.

Work place dust is handled by engineering controls such as air filtration and dust collection systems, but it would be better to eliminate or at least substantially reduce the formation of dust so that the engineering controls in the work place would be a secondary line of defense and not the primary dust-control means.

Accordingly, it would be desirable to provide a plastic SAP particle, which would be more resistant to fracture and disintegration during processing. Humectants, such as glycerol, have been suggested as plasticizers for SAPs. However, because they function well only in the presence of water, their use is impractical as the SAP becomes tacky in the presence of small amounts of water, and is designed to swell and gel in the presence of large amounts of water. Furthermore, water is not a practical plasticizer for SAPs in a commercial setting because the moisture level in the polymer and, consequently, its ductility or brittleness would fluctuate with changes in the relative humidity.

Another proposed dust control technique entails coating the brittle SAP particles with a non-penetrating hydrophilic liquid which would trap the microscopic dust particles as they form and prevent them from becoming airborne during subsequent handling. This approach is described in WO 94/22940, in which various polyethylene oxide adducts used in surface treatments of SAP particles are taught as de-dusting agents. A different approach is disclosed in EP 0 690 077 Al, wherein the fracture mechanics of the SAP particles are modified by using polyethylene oxide functional co-monomers in the conventional acrylic acid polymerization or through a process of solvent exchange, to distribute polyglycols throughout superabsorbent granules. The polyglycol materials are effective in minimizing the generation of polymer fines and aerosol dusts when the dry particles are subjected to high impact and shearing conditions. However, such polyglycol co-monomers are costly specialty chemicals and using them at levels high enough to effectively modify SAP properties would make the resultant SAP economically unattractive. Even the high molecular weight polyethylene oxide polymers which could be solvent-exchanged into the granules cost several times that of the SAP itself.

Accordingly, there is a need in the art for novel approaches for solving the brittleness problems of SAPs. Applicant has now surprisingly discovered that an aqueous dispersion of a rubbery material may be used to successfully overcome the brittleness problem.

SUMMARY OF THE INVENTION

The present invention is directed to a hydrogel-forming polymeric material including a first compound which is a superabsorbent polymer and a second compound including an elastomeric material (i.e., soft, rubbery latex) effective to increase the fracture resistance of the superabsorbent. The second compound is present in the first as a dispersed phase. The first compound includes a water insoluble but water swellable polymer or a carboxylic-functional polyelectrolyte in combination with a crosslinker reactive with carboxyl or carboxylate groups. The second compound includes an effective amount of an aqueous dispersion of a rubbery material.

DETAILED DESCRIPTION OF THE INVENTION

All patents, patent applications and references cited herein are incorporated hereby by reference. In case of inconsistencies, the present disclosure governs.

The present invention provides a cost-effective, improved superabsorbent material having modified fracture mechanics to greatly minimize the formation of dust during the handling of the material. This is accomplished by thoroughly blending the superabsorbent polymer (SAP), at the time of its manufacture, with an elastomeric material which forms a dispersed elastomeric phase thereby lowering the ductile-brittle transition temperature of the SAP to below room temperature so that frequency of spontaneous particle fracture during shipping and handling is greatly diminished. The elastomeric material used in the present invention is a soft latex that has a rubbery appearance upon drying. In the context of this invention, a soft latex is one which is film-forming at room temperature unlike a hard latex which dries to a powder and must be heated above its softening point to become film-forming.

The hydrogel-forming material of the present invention is a blend of at least two immiscible polymers—(1) the superabsorbent polymer (SAP), and (2) the polymer present in an aqueous dispersion of an elastomer, which is combined with the SAP during manufacture. As used herein, the "hydrogel-forming polymeric material" refers to a highly absorbent material having a property of forming a gel upon liquid absorption. A "superabsorbent polymer" is a water soluble polymer which has been crosslinked (for example upon drying and curing with a crosslinkers reactive with a functional group on the polymer or by including a poly-functional comonomer in the polymerization recipe) to render it water insoluble but water swellable.

The preferred SAP of the invention contains a carboxylic-functional polyelectrolyte in combination with a crosslinkers reactive with carboxyl or carboxylate groups. In addition to the SAPs described in the Example, it is contemplated that any polymer which would be water soluble if not crosslinked may be employed. Suitable examples include polyacrylamides, polyvinyl alcohol, ethylene maleic anhydride copolymers, polyvinyl ethers, hydroxypropyl cellulose, carboxymethyl cellulose, polyvinylmorpholinone, polymers and copolymers of vinyl sulfonic acid, polyacrylates, polyacrylamides, polyvinyl pyridine and the like.

Crosslinking agents that may be used for preparing the hydrogel-forming polymeric material of the invention are well known in the art.

Illustrative examples of the polyfunctional crosslinking agents useful in this invention to convert the above water soluble polymers into polyelectrolytes into water-swellable polymers are set forth in U.S. Pat. Nos. 2,929,154; 3,224,986; 3,332,909; and 4,076,673. These polyfunctional crosslinking agents are generally known as polyamide-polyamine epichlorohydrin adducts. Similar crosslinking agents such as commercially available Kymene 557 and Polycup 172 (obtained from Hercules Incorporated, Wilmington, Delaware). The structure of these adducts is well known and is described in M. E. Coor et al., *Journal of Applied Polymer Science*, Vol . 17, pages 721–735 (1973).

Illustrative examples of the difunctional agents useful in this invention are polyhaloalkanols such as 1,3-dichloroisopropanol; 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers having an epoxy equivalent weight range from about 175 to about 380, bisphenol A-epichlorohydrin epoxy resins having an epoxy equivalent weight range from about 182 to about 975 and mixtures of the foregoing.

Also useful as crosslinking agents are monomeric amine-epihalohydrin adducts. Sulfonium zwitterions described in U.S. Pat. Nos. 3,660,43 1; 3,749,737; and 3,749,738, may also be used.

The crosslinking agents may be used in an amount from about 0.05 to about 5.0 percent based on the weight of the polyelectrolyte used. This is generally sufficient to cause the polyelectrolyte to become lightly crosslinked. However, this range may vary for each polyelectrolyte in order to adjust the absorbency of the final crosslinked material and can be determined using routine experimentation. Hydrogel-forming polymer may be prepared directly from crosslinking monomers, such as for example, N,N-methylenebisacrylamide, ethylene glycol diacrylate, triallyl amine, and trimethylolpropane triacrylate. The crosslinking comonomer suitable for use in the present invention has at least two sites of unsaturation capable of copolymerizing with the backbone comonomers during radical-induced polymerization. An especially preferred hydrogel-forming polymer for this invention is crosslinked partially neutralized poly(acrylic acid).

The second component of the hydrogel-forming material of the invention is an elastomeric material which acts to increase the fracture resistance of the SAP. Elastomeric material is added to SAP in an effective amount as an aqueous dispersion. As used herein, an "effective amount" is that amount of elastomer that is effective to increase the fracture resistance of SAP. In one embodiment of the invention, the effective amount is from about 1.0% to about 50% , preferably from about 2.0% to about 25%, and most preferably from about 5% to about 20%.

Representative examples of suitable elastomeric materials are the natural and synthetic latexes which are commonly used as binders and elastomeric adhesives in the fabrication of airlaid absorbent products. In addition to the latexes described in the Examples, its is contemplated that any natural or synthetic elastomer capable of forming a latex dispersion would be suitable for use in the present invention. Thus, natural rubber, polybutadiene rubber, styrene-butadiene rubber, acrylonitrile butadiene rubber, poly-2-chlorobutadiene rubber, polyisoprene rubber, isopreneisobutylene copolymers, ethylene-propylene rubber, ethylene-vinylacetate copolymers, chlorinated polyethylene, chlorosulfonated. polyethylene, acrylic rubber, ethylene-acrylate copolymers, epichlorohydrin rubber, polypropylene oxide rubber and polyurethanes, may be used.

One skilled in the art of polymer processing may prepare the dispersed elastomeric phase of the present invention by emulsifying a solution of an appropriate elastomer in an organic solvent in the aqueous charge to a polymerization reactor followed by stripping the organic solvent prior to charging the monomers. It is additionally understood that any "soft" or elastomeric composition would fall under the scope of this invention, even those which depend on the use of tackifier resins to attain their softness.

In one embodiment of the invention, the hydrogel-forming polymeric material exhibits a gel capacity of at least about 20 grams of 0.9% saline per gram of material and a Friability Index of at least about 25 percent greater than the Friability Index exhibited by an otherwise substantially identical hydrogel-forming polymeric material that is prepared without an elastomer.

The improved hydrogel-forming polymeric material of the present invention may be prepared in at least two ways. In one embodiment, the elastomeric material may be blended with a water soluble pre-polymer, and the pre-polymer is then crosslinked to form the SAP. In another embodiment, the elastomeric material may be blended into a monomer prior to conventional superabsorbent gel polymerization. The elastomer addition must be done before the superabsorbent is crosslinked for example by mixing the elastomeric with the monomer/crosslinking comonomer solution or by mixing the elastomeric with the water soluble polymer/crosslinkers solution.

In one embodiment, a carboxylic-functional polyelectrolyte solution may be prepared by: (i) blending a crosslinkers reactive with carboxyl or carboxylate groups into the polyelectrolyte solution along with an aqueous colloidal dispersion of a rubbery polymeric material; and (ii) drying and sizing the hydrogel-forming polymeric material wherein the particle size distribution is between 75 and 1000 microns and is useful as the superabsorbent additive to absorbent hygienic products.

In another embodiment, a process for preparing a hydrogel-forming material comprises the steps of:

(i) preparing an aqueous solution of carboxylic-functional ethylenically unsaturated monomers along with a suitable polyfunctional crosslinking agent either reactive with the carboxyl or carboxylate group or reactive in radical-induced copolymerization with the aforementioned monomer solution;

(ii) blending into the monomer solution of step (i) an amount of an aqueous colloidal dispersion of a elastomeric material in the amount effective to increase the fracture resistance of the water swellable hydrogel-forming polymeric material;

(iii) initiating the polymerization of the monomer/elastomer blend of step (ii) by known radical-generating techniques; and (iv) drying and sizing the hydrogel-forming polymeric material so that the particle size distribution is substantially within the range of between 75 and 1000 microns.

The invention further relates to a disposable absorbent product prepared with a fracture resistant hydrogel-forming material of the invention. In one embodiment, the disposable absorbent product of the invention comprises a liquid-permeable topsheet, a backsheet attached to the topsheet, and an absorbent structure positioned between the topsheet and backsheet, wherein the absorbent structure comprises a hydrogel-forming polymeric material of the invention. Absorbent articles of the invention may be prepared using techniques well known in the art.

EXAMPLES

The following non-uniting examples demonstrate the preparation and performance of improved SAPs according to the present invention.

Examples 1–5

Preparation of the Type 1 SAP (prepared from soluble polymer as a starting material)

Example 1
Preparation of the Superabsorbent Polymer Precursor Solution

The sodium half salt of poly(isobutylene-co-maleic anhydride) (ISOBAM-10 from Kuraray America, Inc. New York, N.Y. was prepared in a 1000 ml resin flask equipped with paddle stirrer, reflux condenser, temperature controller, and heating mantle at 25% solids by suspending 154 g (1.0 mol) of copolymer in 582 grams of distilled water containing 0.3 grams of Neodol 25-9 (non-ionic surfactant) by Shell Chemical Company, Houston, Texas. Sodium hydroxide in the prill or bead form (40.0 grams, 1.0 mol, from Aldrich Chemical, Milwaukee, Wisconsin) was added to the slurry and the temperature increased to 85° C. Heating and stirring was continued until the polymer dissolved, about 4 hours, to yield a clear viscous solution at 25% solids by weight. To 10.0 grams of the 25% polymer solution was added with rapid stirring 0.25 grams (1% by weight) crosslinkers (KYMENE 557 from Hercules). The solution was poured into an aluminum weighing dish and dried at 125° C. for several hours to form a thick polymer film. This material was used as a control.

Example 2
Preparation of Improved SAP

The preparation of the SAP of Example 1 was repeated but a soft acrylic latex RHOPLEX HA-8 (from Rohm & Haas, Philadelphia, Pennsylvania) was added to the precursor solution before the crosslinkers. HA-8 latex was 45.2% solids. To obtain a SAP having 25% latex solids based on the total polymer weight, 1.88 grams of HA-8 was used. Upon drying, SAP formed an opaque-looking polymer film.

Example 3
Preparation of Improved SAP

The preparation of the SAP of Example 1 was repeated but a soft acrylic latex NW 2744F, (from Rohm & Haas) was added to the precursor solution before the crosslinkers. NW 2744F latex was 47.2% solids. To obtain a SAP having 25% latex solids based on the total polymer weight, 1.85 grams of NW 2744F was used. Upon drying, the SAP formed an opaque-looking polymer film.

Example 4
Preparation of Improved SAP

The preparation of the SAP of Example 1 was repeated but Air Flex 108 (AF-108) latex, (a poly(vinyl acetate)-ethylene copolymer latex, from Air Products, Allentown, Pennsylvania) was added during the initial charge into the reactor. AF-108 latex is 52.3% solids. To obtain a SAP having 25% latex solids based on the total polymer weight, 1.61 grams of AF-108 was added. Upon drying, the SAP formed an opaque-looking polymer film.

Examples 5
Preparation of Improved SAP

The preparation of the SAP of Example 1 was repeated but a hard styrenebutadiene copolymer latex from Gen Corp., Mogadore, Ohio (GEN-FLO 2544 (GF2544)) was mixed with the precursor solution. GF2544 latex was 50% solids. To obtain a SAP having 25% latex solids based on the total polymer weight, 1.65 grams of GF2544 was used.

Test Methods for Evaluation of Experimental Samples

The gel capacity or gel volume of SAPs prepared according to the present Examples 1–5 was determined on the particle size fraction between 300 and 850 microns. A SAP sample (200–300 mg) was weighed to the nearest centigram into a tared absorption cylinder (1.5 inch inside diameter plastic cylinder with a 100 mesh stainless steel screen glued on one end) and the cylinder was placed in a dish of 0.9%

NaCl for one hour. The cylinder was blotted on paper toweling until no more fluid was removed and was then weighed. The gel capacity (grams saline per gram polymer) equals the weight of blotted gel minus the weight of dry sample divided by the weight of dry sample.

SAP Grinding Studies

SAP particles prepared according to the present Examples 1–5, of between 2.8 and 8.0 mm were dried overnight at 72° C. in a laboratory convection oven. A five gram portion was placed in the blender (Osterizer 14 speed) and ground at low speed on the chop setting for 30 seconds and then separated on a stack of standard sieves (20, 30, 60, 200 mesh). The fraction of the sample held on each sieve and the sieve bottom pan was calculated. The thick dry films obtained as described above, about 3.0 grams total weight, were ground in the same manner as the particles. The Friability Index is defined as the ratio of the fraction of particles larger than 850 microns of the sample and the control for that sample. Accordingly, the control would have a Friability Index of 1.0.

TABLE 1

Latex-modified Superabsorbent (Examples 1–5)
(Fractions as Weight Percent)

| Sieve Size Microns | Example 1 Control SAP | Example 2 25% HA-8 | Example 3 25% NW 2744F | Example 4 25% AF-108 | Example 5 25% GF 2544 |
|---|---|---|---|---|---|
| 75 | 14.8 | 4.1 | 3.9 | 12.9 | 17 |
| 250 | 44.1 | 26.4 | 24.8 | 21.6 | 32.4 |
| 600 | 23.0 | 14.5 | 25.1 | 15.2 | 0 |
| 850 | 18.1 | 55.0 | 46.2 | 50.5 | 50.5 |
| Friability | 1.0 | 3.04 | 2.55 | 2.79 | 2.79 |

As shown in Table 1, the control SAP, including no elastomeric latex was brittle and glassy. The improved SAPs of the present invention, made according to Examples 2–4 (containing soft, rubbery latex) demonstrated a shift in particle size distribution toward larger particles as determined in the SAP grinding studies. The hard (non-rubbery) styrene-butadiene copolymer latex of Example 5 (GEN-FLO 2544) appeared to encourage a bimodal distribution (both large and small particles) perhaps by facilitating particle fracture. The dispersed hard particles could be stress-concentrators rather than stress relievers. Humectants may be an alternative way to soften or plasticize polyelectrolytes, although the result may vary widely with moisture level.

Examples 6–11

Effect of Latex Solids on Gel Capacity

It is known in the art that fillers reduce the absolute absorbency of the modified superabsorbent on a weight percent basis. To determine the effect of latex on absorption capacity (gel capacity) of SAP, SAP material was prepared according to Example 1 and the latex was added in varying amounts. Latex solids by weight was 5% HA-8 (Example 6); 10% HA-8 (Example 7); 15% HA-8 (Example 8); 20% HA-8 (Example 9); 25% HA-8 (Example 10); 50% HA-8 (Example 11). The results of grinding studies and measurement of gel capacity on the experimental SAPs are set forth in Table 2 below.

TABLE 2

HA-8 Latex-modified Superabsorbent (Examples 6–11)

|  | Ex. 1 | Example 6 | Example 7 | Example 8 | Example 9 | Example 10 | Example 11 |
|---|---|---|---|---|---|---|---|
| Microns | Control | 5% HA-8 | 10% HA-8 | 15% HA-8 | 20% HA-8 | 25% HA-8 | 50% HA-8 |
| 75 | 14.8 | 11.9 | 8.9 | 6.6 | 5.4 | 4.1 | 1.4 |
| 250 | 44.1 | 39.8 | 35.6 | 29.3 | 24.1 | 26.4 | 8.5 |
| 600 | 23 | 22.2 | 19.1 | 17.1 | 13.2 | 14.5 | 10.1 |
| 850 | 18.1 | 26.1 | 36.4 | 46.9 | 57.4 | 55 | 80.1 |
| Friability | 1.0 | 1.44 | 2.01 | 2.59 | 3.17 | 3.04 | 4.43 |
| Gel. Cap. | 25.9 | 24.2 | 25.5 | 21.5 | 22.2 | 17.4 | 10.5 |

Referring to Table 2, even as little as 5% by weight of the soft latex reduces the amount of fine (75 microns) and increases the distribution of large particles. In addition, no significant decrease in gel capacity is seen at up to about 10% latex.

Examples 12–16

Preparation of Type 2 SAP (prepared from monomers as a starting material)

Example 12

Preparation of Granular Acrylic Superabsorbent

A crosslinked gel of 75% neutralized poly(acrylic acid) was prepared as a control material as follows: A one-liter capacity resin reactor with a four-port top was assembled with a stirrer, nitrogen inlet, air-cooled condenser, and a stainless steel thermistor probe. The reactor was mounted in a 2 liter beaker heating mantle which was also equipped with compressed air cooling connected through the electronic temperature controller. The set point was 70° C. and the nitrogen gas flow rate was adjusted to 100 milliliters per minute. The reactor was charged sequentially with 154 grams of distilled water, 15.0 grams (0.375 mol) sodium hydroxide, 36 grams (0.5 mol) acrylic acid, and 0.77 grams (0.005 mol) N,N'-methylenebisacrylamide washed into the reactor with 10 grams of water. The nitrogen purge was begun and the temperature controller turned on. When the reactor contents reached 65° C., sodium persulfate (0.2 grams, 0.0084 mole) was added in 10 grams of water. After the reactor contents gelled (3–5 minutes), the stirrer and temperature controller were turned off and the gel allowed to sit in the reactor for 30 minutes. The reactor was opened and the gel cut into 1–2 cm chunks for drying in a 125° C. convection oven. The recipe yielded 45 grams of poly (acrylate) superabsorbent. The oven dried polymer pieces are sharp and highly irregular. They were gently ground in a laboratory blender and the fraction passing a screen with 8.0 mm openings and held on a screen with 2.8 mm openings was set aside for fracture resistance studies. This material was used as a control.

Examples 13–16

The SAP material of Examples 13–16 was prepared according to Example 12 except that latex was added before the monomer was polymerized. Varying amounts of AF-108 were used. For example 13, 5% latex solids based on total polymer in the blend were used. (4.5 grams of latex, nominally about 50% solids by weight, was required.) For Example 14, 10% dispersed elastomer was used and required 9.6 grams of latex. For Example 15, 15% dispersed elastomer was used and required 15.2 grams. For Example 16, 25% dispersed elastomer was used and required 28.7 grams of latex.

TABLE 3

Type Two SAPs (Examples 12–16)

| | Example 12 | Example 13 | Example 14 | Example 15 | Example 16 |
|---|---|---|---|---|---|
| % AF-108 Latex | control | 5 | 10 | 15 | 25 |
| Gel Capacity g/g | 27.1 | 25.5 | 19.9 | 19.9 | 16.7 |
| <75 microns | 1.1 | 1.2 | 0.8 | 0.3 | 0.3 |
| 75 | 20.9 | 19.0 | 15.3 | 12.6 | 9.9 |
| 250 | 50.8 | 41.8 | 35.3 | 29.7 | 23.6 |
| 600 | 17.0 | 19.1 | 20.5 | 17.5 | 15.9 |
| 850 | 10.2 | 18.9 | 28.0 | 39.8 | 50.4 |
| Friability | 1.0 | 1.34 | 2.75 | 3.9 | 4.94 |

Table 3 shows that the absorbency (gel capacity) of the blends decreases as the proportion of latex component in the mixture increases. In the size distribution study, the fractions represent weight percent of the sample trapped on each size screen. As little as 5% latex solids in the blend significantly increases the distribution of large particles remaining after the standard grinding, indicating a tougher or more resilient material. At 10% latex solids, the small particle fraction is decreased and the large particle fraction is greatly increased.

Examples 17–20
Effect of Change in Proportions of Thickener

The preparation of SAPs according to Example 12 was repeated except that the batch size was doubled and the molar amount of crosslinkers was reduced by 50%. To determine the effect of thickening the monomer solution, 1.0 gram of a high molecular weight polyacrylamide was dissolved in the water. The advantage of having the monomer solution thickened is that thickening helps coating application after initiation but before gelation.

TABLE 4

Fracture Resistant Superabsorbent Granules Prepared from Monomer (Double batch, half crosslinkers - Examples 17–20)

| | Example 17 | Example 18 | Example 19 | Example 20 |
|---|---|---|---|---|
| % Latex | 0 | 0 | 15 | 15 |
| % Thickener | 0 | 1.1 | 0 | 1.1 |
| Gel Capacity g/g | 34.0 | 30.2 | 28.5 | 25.2 |
| <75 Microns | 0.3 | 1.0 | 0.2 | 0.8 |
| 75 | 18.1 | 18.4 | 12.7 | 16.1 |
| 250 | 54.8 | 49.6 | 30.8 | 31.2 |
| 600 | 19.8 | 19.1 | 20.0 | 15.4 |
| 850 | 7.1 | 11.9 | 36.3 | 36.5 |
| Friability | 1.0 | 1.0 | 5.11 | 3.07 |

The above represented results show that the inclusion of a fracture-resistant agent in the polymer formulation enables the modified superabsorbent to suffer far less comminution than the respective controls under identical grinding conditions. The presence of the polyacrylamide thickener and reducing the crosslinkers level had little effect on the fracture pattern (comparing Table 4 to Example 15 in Table 3). Reducing the crosslinkers level has the expected effect of increasing the gel capacity of the polymer.

What is claimed is:

1. A hydrogel-forming polymeric material comprising a first compound which is a superabsorbent polymer and a second compound present in the first as a dispersed phase comprising an elastomeric material effective to increase the fracture resistance of the superabsorbent prepared from:
   a. a first compound comprising carboxylic-functional polyelectrolytes in combination with a crosslinker reactive with carboxyl or carboxylate groups; and
   b. an effective amount of a second compound comprising an aqueous dispersion of a rubbery material, wherein the hydrogel-forming polymeric material exhibits a gel capacity of at least about 20 grams 0.9% saline per gram of material and a Friability Index of at least about 25% greater than the Friability Index exhibited by a hydrogel-forming polymeric material that is prepared without the second compound.

2. The hydrogel-forming polymeric material of claim 1 wherein the first compound is selected from the group consisting of poly(acrylic acid), poly(methacrylic acid), poly(isobutylene-alt-maleic anhydride), poly(styrene-alt-maleic anhydride, carboxymethyl cellulose or starch, and mixtures and copolymers thereof which has been crosslinked by reaction with a crosslinkers reactive with carboxyl or carboxylate groups.

3. The hydrogel-forming polymeric material of claim 1 wherein the second compound is a latex prepared by polymerizing ethylenically unsaturated monomers selected from the group consisting of alkylacrylates and methacrylates, styrene, butadiene, isoprene, acrylonitrile, vinyl acetate, and ethylene, and copolymers thereof.

4. The hydrogel-forming polymeric material of claim 3 wherein the minimum film-forming temperature of the second compound is not greater than about 25° C. such that the second compound is elastomeric at room temperature.

5. The hydrogel-forming polymeric material of claim 1 wherein the second compound is a natural rubber latex.

6. The hydrogel-forming polymeric material of claim 1 wherein the second compound is used in an amount that is greater than 0 to about 100 weight percent of the first compound used.

7. The hydrogel-forming polymeric material of claim 1 wherein the second compound is used in an amount that is greater than 0 to about 25 weight percent of the first compound used.

8. A hydrogel-forming polymeric material comprising a first compound which is a superabsorbent polymer and a second compound present in the first as a dispersed phase comprising an elastomeric material effective to increase the fracture resistance of the superabsorbent prepared from the steps of:
   (i) preparing an aqueous solution of carboxylic-functional ethylenically unsaturated monomers and a suitable polyfunctional crosslinking agent, said crosslinking agent being reactive with the carboxyl or carboxylate groups or reactive in radical-induced copolymerization with the monomer solution;
   (ii) blending an amount of an aqueous colloidal dispersion of a rubbery polymeric material into the aqueous solution obtained in step (i), said amount being effective to increase the fracture resistance of the water swellable hydrogel-forming polymeric material; and
   (iii) initiating the polymerization of the aforementioned monomer/rubber blend.

9. The hydrogel-forming polymeric material of claim 8 wherein the first compound is a polymer or copolymer prepared from monomers selected from the group consisting of acrylic acid, methacrylic acid, crotonic acid, itaconic acid, maleic acid and its anhydride, the salts of the foregoing acidic monomers, and any ethylenically unsaturated monomer copolymerizable with the foregoing monomers, and a poly-functional comonomer capable of crosslinking the foregoing polymers and copolymers during the polymerization step.

10. A disposable absorbent product comprising a liquid-permeable topsheet, a backsheet attached to the topsheet, and an absorbent structure positioned between the topsheet and the backsheet, wherein the absorbent structure comprises a hydrogel-forming polymeric material prepared from:
   a. a first compound which is a superabsorbent polymer; and
   b. a second compound present in the first as a dispersed phase comprising a elastomeric material effective to increase the fracture resistance of the superabsorbent
   wherein the hydrogel-forming polymeric material exhibits a gel capacity of at least about 20 grams 0.9% saline per gram of material and a Friability Index of at least about 25% greater than the Friability Index exhibited by hydrogel-forming polymeric material that is prepared without the second compound.

11. The process of claim 10 in which the aqueous dispersion of rubbery material is a natural rubber latex.

12. The process of claim 10 in which the aqueous dispersion of rubbery material is a synthetic latex prepared from ethylenically unsaturated monomers selected from the group comprising: alkylacrylates and methacrylates, styrene, butadiene, isoprene, acrylonitrile, vinyl acetate, and ethylene and copolymers thereof.

13. The process of claim 10 in which the aqueous dispersion of rubbery material is a natural rubber latex.

14. The process of claim 10 in which the aqueous dispersion of rubbery material is a synthetic latex prepared from ethylenically unsaturated monomers selected from the group comprising: alkylacrylates and methacrylates, styrene, butadiene, isoprene, acrylonitrile, vinyl acetate, and ethylene and copolymers thereof.

15. A process for preparing a hydrogel-forming polymeric material comprising preparing a carboxylic-functional polyelectrolyte solution by
   a. blending a crosslinker reactive with carboxyl or carboxylate groups into the polyelectrolyte solution along with an aqueous colloidal dispersion of a rubbery polymeric material;
   b. drying and sizing the hydrogel-forming polymeric material wherein the particle size distribution is between 75 and 1000 microns and is useful as the superabsorbent additive to absorbent hygienic products.

16. A process for preparing a hydrogel-forming material comprising the steps of:
   (i) preparing an aqueous solution of carboxylic-functional ethylenically unsaturated monomers and a suitable polyfunctional crosslinking agent, said crosslinking agent being reactive with the carboxyl or carboxylate groups or reactive in radical-induced copolymerization with the monomer solution;
   (ii) blending an amount of an aqueous colloidal dispersion of a rubbery polymeric material into the aqueous solution obtained in step (i), said amount being effective to increase the fracture resistance of the water swellable hydrogel-forming polymeric material; and
   (iii) initiating the polymerization of the aforementioned monomer/rubber blend.

* * * * *